United States Patent [19]

Heiba

[11] Patent Number: 4,528,145
[45] Date of Patent: Jul. 9, 1985

[54] HERBICIDAL N-SUBSTITUTED-5(SUBSTITUTED-PHENOXY)-2-SUBSTITUTED BENZOIC ACID SULFAMIDOYL FLUORIDE

[76] Inventor: El-Ahmadi I. Heiba, 11 Balsam La, Princeton, N.J. 08540

[21] Appl. No.: 422,585

[22] Filed: Sep. 24, 1982

[51] Int. Cl.³ .......................................... C07C 149/43
[52] U.S. Cl. ................................ 260/543 F; 71/87; 71/98; 71/103; 260/453 RZ; 260/465 D; 260/935; 560/16
[58] Field of Search ............ 260/543 F; 71/103; 560/16

[56] References Cited

U.S. PATENT DOCUMENTS

| | | | |
|---|---|---|---|
| 2,337,532 | 12/1943 | Thomas | 260/543 F |
| 2,911,439 | 11/1959 | Meikle | 260/543 F |
| 3,050,556 | 8/1962 | Van Dyke Tiers | 260/543 F |
| 3,453,099 | 7/1969 | Popoff et al. | 260/543 F |
| 3,919,308 | 11/1975 | Hamprecht | 71/103 |
| 4,093,446 | 6/1978 | Bayer et al. | 71/103 |
| 4,246,419 | 1/1981 | Cartwright et al. | 71/103 |
| 4,285,723 | 8/1981 | Cartwright et al. | 71/103 |
| 4,311,514 | 1/1982 | Szczepanski et al. | 71/103 |

FOREIGN PATENT DOCUMENTS

| | | | |
|---|---|---|---|
| 407318 | 4/1965 | Japan | 71/103 |
| 872670 | 7/1961 | United Kingdom | 260/543 F |

*Primary Examiner*—Glennon H. Hollrah
*Assistant Examiner*—Raymond Covington
*Attorney, Agent, or Firm*—Sixbey, Friedman & Leedom

[57] ABSTRACT

N-substituted-5-(substituted-phenoxy)-2-substituted benzoic acid sulfamidoyl fluoride their preparation and use as herbicides are disclosed.

5 Claims, No Drawings

HERBICIDAL N-SUBSTITUTED-5(SUBSTITUTED-PHENOXY)-2-SUBSTITUTED BENZOIC ACID SULFAMIDOYL FLUORIDE

BACKGROUND OF THE INVENTION

Herbicidal 5-(2-chloro-4-trifluoromethyl)-phenoxy-2-nitrobenzoic acid and salts thereof, and various herbicidal derivatives of these compunds have been proposed including alkyl and cycloalkyl esters, alkylthio esters, phenyl ester, alkyl and dialkyl amido and benzoyl chloride forms. U.S. Pat. Nos. which describe such compounds and the like include 3,652,645; 3,784,635; 3,873,302; 3,983,168; 3,907,866; 3,798,276; 3,928,416; and 4,063,929. Recent U.S. Pat. No. 4,285,723 which disclose N-sulphonyl-3-phenoxybenzamide derivatives and their salts as herbicides.

SUMMARY OF THE INVENTION

This invention provides certain herbicidal compounds of the formula:

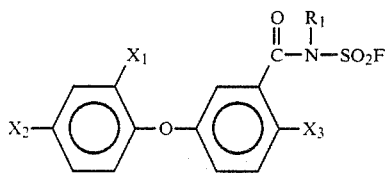

wherein
$R_1$ is H; an agronomically acceptable cation M; halogen, preferably chlorine; sulfenyl group cf the general formula $SR_2$; thiosulfenyl group of the general formula $S-SR_2$; sulfinyl group of the general formula

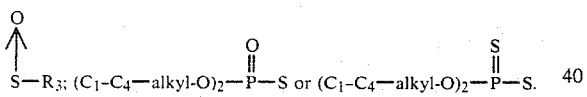

Examples of $R_2$ include $C_1-C_4$-alkyl; $C_1-C_4$-alkyl substituted with one or more of Cl, Br, F, COOH, COO—alkyl ($C_1-C_4$), CN, etc.; $CCl_3$; $CF_3$; $CFCl_2$; $CF_2Cl$; substituted or unsubstituted cycloalkyl; substituted or unsubstituted heterocycle (e.g. having from 5 to 7 atom); substituted or unsubstituted phenyl, cyano; $C_1-C_4$-dialkylamino; substituted or unsubstituted diphenylamino; COOH; COO—alkyl ($C_1-C_4$), etc. Examples of $R_3$ include $C_1-C_4$-alkyl; $C_1-C_4$-alkyl halogenated with more than one halogen.

$X_1$, $X_2$, and $X_3$, are substituents capable of imparting herbicidal properties. Suitable substituents include halogen, such as F, Cl, and Br; polyhaloalkyl, such as $CF_3$; $NO_2$; CN; alkyl; alkoxy; $SO_2$ alkyl; $SO_2NH_2$; NO; COO—alkyl and the like in which the alkyl and alkoxy groups preferably contain 1 to 4 carbon atoms.

Compounds in which $X_1$ is Cl, and $X_2$ is $CF_3$ are preferred. An exemplary compound has the Formula I in which $X_1$ is Cl, $X_2$ is $CF_3$, $X_3$ is $NO_2$, and $R_1$ is an agronomically accepted cation. Another exemplary compound with excellent systemic herbicidal activity has the Formula I in which $X_1$ is Cl, $X_2$ is $CF_3$, $X_3$ is $NO_2$, and $R_1$ is Cl or $SCl_3$ or $SCOOCH_3$.

The compounds of this invention can be easily prepared from appropriate precursor by methods known in the art although it is believed that these methods have not previously been applied to make compounds of the present invention. The compounds of this invention having Formula I in which $R_1$ is H can be prepared in good yields by reacting the appropriate aryloxy benzoic acid chloride with amidosulfuryl fluoride $NH_2SO_2F$. The reaction can be conducted by heating the reactants in the temperature ranges 50°-200°, preferably between 110°-150°. The reaction can be affected by heating the mixed reactants per se or in inreactive solvents for example chlorobenzene, toluene and dichlorobenzene and the like. The above mentioned reaction can be conducted in the absence of an acid acceptor, although in certain instances it might be desirable to use one mole equivalent of an acid acceptor such as pyridene, quinoline, trimethyl amine, tri-ethylamine and the like. The products having Formula I can be separated and purified by usual methods known to those skilled in the art.

Another useful method which can be used to prepare the compounds of this invention having Formula I in which $R_1$ is H and that is to react the appropriate aryloxyl benzoic acid amide with oxalyl chloride to form the corresponding carbonyl isocyanate i.e. compounds having the

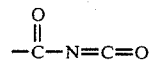

moiety attached adjacent to $X_3$ in the diphenylether nucleus in Formula I. The carbonyl isocyanate precursors prepared in the above described and known manner are then reacted with flourosulfonic acid $HO-SO_2F$ to yield the corresponding sulfamidoyl fluoride of Formula I in which $R_1$ is H. The overall reaction sequences may be illustrated as follows:

$$-\overset{O}{\underset{\|}{C}}-NH_2 \xrightarrow{C_2O_2Cl_2} -\overset{O}{\underset{\|}{C}}-N=C=O + 2HCl \xrightarrow{HOSO_2F}$$

$$-\overset{O}{\underset{\|}{C}}-\overset{H}{\underset{|}{N}}SO_2F + CO_2$$

The compounds of this invention having Formula I in which $R_1$ is H are acidic in properties and react readily with alkali metal hydroxide or alkoxide as well as organic bases such as alkylamine, dialkylamine or trialkylamine and the like to form the corresponding salt. The salt form of the compounds of this invention, i.e. where $R_1$ is M are stable compounds readily soluble in water, alcohols and polar solvents; indicative of their desirable lipophilic properties. The compounds of this invention in which $R_1$ is halogen (particularly chloro) can be easily prepared by methods known in the art:

(a) by the direct chlorination of compounds of Formula I in which $R_1$ is H with sodium hypochlorite, hypochlorous acid or t-BuOCl, following the teaching of F. D. Chattaway, Journal Chemical Society, 87, 145-171 (1905) and H. S. Raper et al., Journal Chemical Society, 85, 371-376 (1903). The chlorination is easily affected by stirring the reactant in a sodium hypochlorite solution at room temperature for few hours. The PH of the reaction mixture is then adjusted to about PH-5 by the addition of acetic acid dropwise. The appropriate N-Chloroproduct of this invention usually precepitates as a solid in almost quantitative yield at about PH-6.5.

(b) by reacting the appropriate aryloxyl benzoic acid chloride with N-Chloro-N-sodiosulfamidoyl fluoride NaNCl-SO$_2$F which can be prepared following the teaching of F. E. Hardy Journal Chemical Society (C) 2087 (1970). Those reactions are illustrated as:

The above described reaction can be conveniently affected by adding the appropriate aryloxyl benzoic acid chloride to an aqueous solution of one mole equivalent of NaNClSO$_2$F while stirring at room temperature for few hours. The precepitated N-Chloroderivative can be washed with cold 5 per cent solution of sodium bicarbonate, filtered and air dried. The N-Chloroderivatives of this invention are very soluble in chlorinated solvents such as dichloromethane, chloroform and carbon tetrachloride and the like.

The compounds of this invention in which R$_1$ is a sulfenyl group can be easily prepared by reacting one molar proportion of the appropriate sulfenyl chloride R$_2$SCl with the compounds of this invention in which R$_1$ is H in the presence of an acid acceptor following the general procedure discussed by F. A. Davis, International Journal/Sulfur Chemistry, Vol. 8, No. I, P. 71 (1973). The overall reaction can be illustrated by:

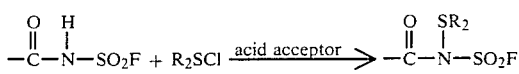

The sulfenyl chloride reactant R$_2$SCl can be easily prepared from known precursors following the teaching of N. Kharasch, Chemical Review, 39, 269 (1946). For the preparation of sulfenyl chloride reactant R$_2$SCl in which R$_2$ is a disubstituted-amino (>N—SCl) it is advantageous to follow the method of Wolfgang H. Mueller & Peter E. Buttler, Journal Organic Chemistry, Vol. 33, No. 5, 2114 (1968), and G. Weiss, German Pat. No. 1,153,744 (1966).

Compounds of this invention having the sulfenyl group as —SCOO—alkyl can be advantageously prepared in the known manner and that by reacting at least one mole equivalent of Carbonyl-sulfide dichloride Cl—S—COCl with the appropriate aryloxyl benzoic acid sulfamidoyl fluoride, dispersed or dissolved in an inreactive solvent such as tetrahydrofuran, dialkyl ether, dichloromethane and the like in the presence of not less than one mole equivalent of an acid acceptor. The above described reaction proceeds readily at room temperature, or lower, and is usually complete in 1-6 hours, after which time excess alcohol such as methanol is added preferably in the presence of added acid acceptor. The overall reaction can be illustrated as:

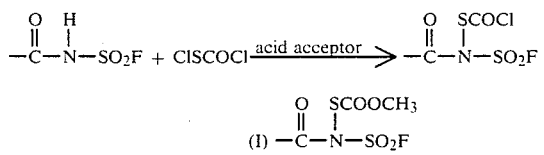

The compounds of this invention having Formula I in which R$_1$ is a sulfinyl group of the general structure SR$_3$ can be easily prepared by reacting the alkylsulfinyl chloride

with the appropriate aryloxyl benzoic acid sulfamidoyl Fluoride. The alkylsulfinyl chloride can be easily prepared from known precursor by the method of I. B. Douglass and D. R. Poole, Journal Organic Chemistry, 22, 536 (1957). The above described reaction can be conveniently carried out in inreactive solvent such as dichloromethane and the like in the presence of an acid acceptor. The reaction may be illustrated as:

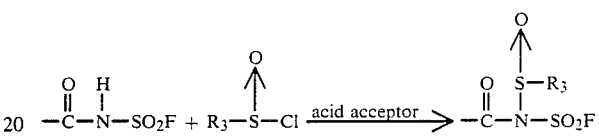

The products of this invention having Formula I in which

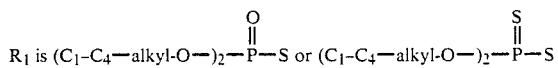

can be easily prepared by reacting the, known, corresponding sulfeny chloride

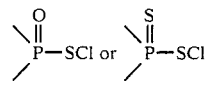

with the appropriate aryloxyl benzoic acid sulfamidoyl fluoride. The above reaction can be carried out in inreactive solvent in the presence of an acid acceptor. The separation and purification of the compound of this invention, from the reaction can be achieved by following procedures known to those skilled in the art.

HERBICIDAL PROPERTIES & APPLICATION

The compounds of this invention having Formula I are lipophilic in properties and translocate readily in weed plants but are biochemically safe to crop plants such as soybean, peanut and cotton. Unlike the N-sulphonyl-3-phenoxybenzamide derivatives, disclosed in the published U.S. Pat. No. 4,285,723 which have an undesirable toxic carry-over effect to the crop plants grown during the subsequent season. For example there are evidences for damages occuring to winter wheat grown in soybean fields previously treated with the above mentioned herbicides. The herbicides of this invention having Formula I are expected to have no carry-over toxic effect because of their relatively rapid degradation in the soil. The compounds of this invention can be advantageously employed as herbicides and various crops for example, soybeans, cotton, and peanuts. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents gases compressed to the liquid state, odorants, stabilizers, and the like. A wide variety of liquid and solid carriers including talc, bentonite, diatomaceous earth pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice herbicidal application is measured in terms of pounds of herbicide applied per acre. The compounds of this invention are effective herbicides when applied in herbicidal amounts, e.g., at rates between about 0.03 pound and about 10 pounds per acre.

EXAMPLE I

Preparation of N-sulfonyl fluoride-5[(2-chloro-4-trifluoromethyl)-phenoxy-]-2-nitro-benzamide (Formula I wherein $R_1$ is H) $X_2$ is $CF_3$, $X_1$ is Cl and $X_3$ is $NO_2$ 5-[(2-chloro-4-trifluoromethyl)-phenoxy]-2-nitro-benzoic acid chloride, 0.05 mole and amidosulfury fluoride, 0.055 mole are mixed in a flask and heated in oil bath about 120°, at which temperature hydrogen chloride gas starts to evolve. The temperature of the reaction mixture is raised to about 140° and kept at this temperature till the hydrogen chloride gas ceases to evolve (about 2 hours). The reaction mixture is cooled dissolved in dichloromethane or chloroform, washed with cold water and dried over anhydrous sodium sulfate. The solvent is evaporated leaving a solid which can be characterized as the sulfamidoyl fluoride of -5-[-(-2chloro-4-trifluoromethyl)-phenoxy]-2 nitro-benzoic acid.

EXAMPLE II

Preparation of the triethylamine salt of N-sulfonyl fluoride-5[-(2-chloro-4-trifluoromethyl)-phenoxy]-2 nitrobenzamide The reaction product from example I, 0.05 mole is dissolved in diethyl ether and 0.05 mole of triethylamine is added dropwise. The ether solvent is evaporated to leave the triethylamine salt as a solid. The triethylamine salt is soluble in water and alcohols. The aqueous solution of the triethylamine salt is stable, assuming the pH of the solution is not higher than pH 10.

EXAMPLE III

Preparation of N-chloro-5-[-(2-chloro-4-trifluoromethyl)-phenoxy ]-2-nitro-benzoic acid sulfamidoyl fluoride The reaction product from example I, 0.05 mole is dissolved, at room temperature, in water containing 0.05 mole sodium hydroxide. Sodium hypochlorite solution is added dropwise while stirring is continued. The pH of the reaction mixture is adjusted to pH 5 by the addition of acetic acid dropwise. The reaction mixture is stirred for an additional one hour, filtered and the N-chloro-solid-product is washed with ice cold water and air dried. The N-chloro-product is soluble in dichloromethane and chloroform and likerates iodine from KI solution quantitatively.

EXAMPLE IV

Preparation N-trichlomethylsulfenyl-5[-(2-chloro-4-trifluoromethyl)-phenoxy]-2-nitro-benzoic acid sulfamidoyl fluoride The reaction product from example I, 0.05 mole is neutralized with 0.05 mole of NaOH aqueous solution. Trichloromethyl sulfenyl chloride, 0.05 mole is added to the reaction mixture while stirring. Stirring is continued for about 2 hours and the reaction mixture is filtered and the solid is washed with ice cold water then air dried. The air-dried product is washed with cold carbon tetrachloride. The reaction product can be dissolved in ether, dichloromethane and chloroform and is unstable in hydrochloric acid solution.

EXAMPLE V

Preparation of N-methylsulfenyl-5[-(2-chloro-4-trifluoromethyl)-phenoxy]-2-nitro-benzoic acid sulfamidoyl fluoride The reaction product obtained from example I, 0.05 mole is dissolved in anhydrous tetrahydrofuran to which t-BuOK, 0.05 mole is added during stirring to convert the product from example I into the corresponding potassium salt. Methylsulfenyl chloride 0.05 mole, dissolved in dichloromethane is added dropwise, to the reaction mixture while maintaining the temperature of the reaction mixture at about 0°. Stirring is continued for additional 6 hours and then the reaction mixture is filtered, to remove KCl, and the solvents are evaporated on a rotary evaporator to leave the N- Methylsulfenyl product as a solid. The reaction product is stable in organic solvents but decomposes in aqueous hydrochloric acid solution.

EXAMPLE VI

Preparation of N-carboxymethylsulfenyl-5[-(2-chloro-4-trifluoromethyl)-phenoxy]-2-nitro-benzoic acid sulfamidoyl fluoride The potassium salt of the product obtained from example I, 0.05 mole, is made in accordance with the method described in example V. To that reaction mixture carbonylsulfide dichloride Cl—S—COCl, 0.05 mole dissolved in dichloromethane is added dropwise. The reaction mixture is stirred for an additional 3 hours, then anhydrous methanol containing $CH_3ONa$, 0.05 mole, is added dropwise while stirring is continued for an additional 2 hours while maintaining the reaction temperature at about 20°. The reaction mixture is filtered to remove NaCl and KCl and then the solvents are evaporated. The carboxymethylsulfenyl product can be obtained in almost quantitative yield. The product is soluble in chlorinated organic solvents, ethers and the like but decomposes in strong aqueous alkaline or acid solutions.

EXAMPLES OF APPLICATIONS

EXAMPLE VII

An emulsifiable concentrate is composed of 10 parts by weight of each of the reaction products from Examples II, III, IV, V and VI, 80 parts by weight of dichloromethane as solvent, and 10 parts by weight of nonylphenol (10 EO) as emulsifier.

EXAMPLE VIII

A mixture of weeds and some crops are sown in vessels having a diameter of 29×22×6 cm. charged with earth and the seeds are covered with earth. The vessels are watered and kept outdoors during the Summer Growing Season. One week after the crop plants and the weeds have emerged, the herbicidal composition cited in example VII, which is emulsified in water, and sprayed in such a way that the crop and weed plants are fully wetted. Two weeks after the treatment, the results show that the product according to this invention has a very good herbicidal activity, when applied, at the rate of 0.5 lb/acre, or lower, in a post-emergence application against broad-leaf and grass weeds while simultaneously has excellent preserving effect for crop plants, soybean and cotton.

EXAMPLE IX

A wettable powder easily dispersible in water is obtained by mixing 25 parts by weight of the reaction product obtained from example IV as active ingredient, 64 parts by weight of kaolin containing quartz as inert substance, 10 parts by weight of potassium salt of ligninsulfonic acid, 1 part by weight of sodium salt of oleymethyltaurine as wetting and dispersing agent and by grinding it.

EXAMPLE X

A mixture of weeds and some crop plants are sown in vessels having a dimension of 29×22×6 cm. charged with earth, and the seeds are covered with earth. The same day the herbicidal composition, cited in example IX, which has been emulsified in water is sprayed on the surface of the soil. The vessels are kept outdoors, during the summer growing season. Three weeks after treatment, the results show that the product according to this invention has very good herbicidal activity against broadleaf weeds and grasses when applied at the rate of about one lb/acre or less and simultaneously there is excellent preserving effect for the crop plants, soybean and cotton.

Although the present invention has been described with preferred embodiments, it is to be understood that modifications and variations may be resorted to, without departing from the spirit and scope of this invention, as those skilled in the art will readily understand. such modifications are considered to be within the purview and scope of the appended claims.

I claim:

1. A compound having herbicidal activity of the formula

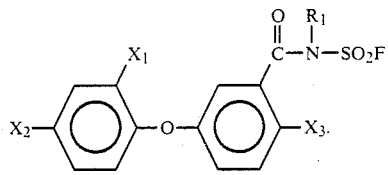

wherein
$R_1$ is a moiety conferring biochemical lability on the resulting fluoride and is selected from H and salts thereof; chlorine; and sulfenyl moiety ($SR_2$) in which $R_2$ is methyl, polyhalomethyl, COO—alkyl ($C_1$–$C_4$), or $C_1$–$C_4$-dialkylamino;

$X_1$, $X_2$, $X_3$ are herbicidal properties imparting substituents selected from halogen, polyhalomethyl, $NO_2$, CN, ($C_1$–$C_4$)alkyl and ($C_1$–$C_4$) alkoxy.

2. A compound in accordance with claim 1 wherein $X_3$ is nitro and $X_1$ and $X_2$ are selected from halogen and polyhalomethyl.

3. A compound in accordance with claim 1 wherein $X_3$ is nitro and $X_1$ and $X_2$ are selected from halogen and polyhalomethyl.

4. A compound in accordance with claim 1 in which $X_1$ is Cl; $X_2$ is $CF_3$; and $X_3$ is $NO_2$.

5. A compound in accordance with claim 1 wherein $R_1$ is H and salts thereof.

* * * * *